United States Patent
Liu (10) Patent No.: US 11,583,701 B2
(45) Date of Patent: Feb. 21, 2023

(54) NEUTRON CAPTURE THERAPY SYSTEM

(71) Applicant: NEUBORON MEDTECH LTD., Jiangsu (CN)

(72) Inventor: Yuan-hao Liu, Jiangsu (CN)

(73) Assignee: NEUBORON MEDTECH LTD., Jiangsu (CN)

(*) Notice: Subject to any disclaimer, the term of this patent is extended or adjusted under 35 U.S.C. 154(b) by 239 days.

(21) Appl. No.: 16/880,125

(22) Filed: May 21, 2020

(65) Prior Publication Data
US 2021/0001151 A1   Jan. 7, 2021

Related U.S. Application Data

(63) Continuation of application No. PCT/CN2018/100987, filed on Aug. 17, 2018.

(30) Foreign Application Priority Data

Dec. 18, 2017 (CN) .......................... 201711365076.4
Dec. 18, 2017 (CN) .......................... 201721777784.4

(51) Int. Cl.
*A61N 5/10* (2006.01)
*H05H 3/06* (2006.01)

(52) U.S. Cl.
CPC .......... *A61N 5/1049* (2013.01); *A61N 5/1045* (2013.01); *A61N 5/1077* (2013.01);
(Continued)

(58) Field of Classification Search
CPC ............ A61N 2005/109; A61N 5/1077; A61N 2005/1094; A61N 5/1064; A61N 5/1071;
(Continued)

(56) References Cited

U.S. PATENT DOCUMENTS 4,223,227 A   9/1980   Horwitz
4,293,771 A   10/1981   Lescrenier
(Continued)

FOREIGN PATENT DOCUMENTS

CN   102985981 A   3/2013
CN   105120952 A   12/2015
(Continued)

OTHER PUBLICATIONS

International Search Report of PCT/CN2018/100987, dated Nov. 7, 2018.
(Continued)

*Primary Examiner* — Christine H Matthews
(74) *Attorney, Agent, or Firm* — Locke Lord LLP; Tim Tingkang Xia, Esq.

(57) ABSTRACT

A neutron capture therapy system includes a neutron beam generating unit, an irradiation room configured to irradiate an irradiated body with a neutron beam, a preparation room configured to implement preparation work required to irradiate the irradiated body with the neutron beam, and an auxiliary positioner disposed in the irradiation room and/or the preparation room. The irradiation room includes a first shielding wall, a collimator is disposed on the first shielding wall for emitting the neutron beam, and the neutron beam is emitted from the collimator and defines a neutron beam axis. The auxiliary positioner includes a laser emitter that emits a laser beam to position the irradiated body, wherein the position of the laser emitter is selectable. Therefore, the irradiated body can be positioned in any case to implement precise irradiation.

18 Claims, 5 Drawing Sheets

(52) U.S. Cl.
CPC ......... *H05H 3/06* (2013.01); *A61N 2005/105* (2013.01); *A61N 2005/109* (2013.01); *A61N 2005/1087* (2013.01); *A61N 2005/1094* (2013.01)

(58) Field of Classification Search
CPC ... A61N 5/1079; A61N 2005/105; H05H 3/06
See application file for complete search history.

(56) References Cited

U.S. PATENT DOCUMENTS

| | | | | |
|---|---|---|---|---|
| 6,275,564 | B1* | 8/2001 | Ein-Gal | A61N 5/1049 378/68 |
| 2007/0131876 | A1* | 6/2007 | Brahme | A61N 5/10 250/492.1 |
| 2008/0122936 | A1* | 5/2008 | Lomnes | H04N 5/2251 348/E5.025 |
| 2012/0174317 | A1* | 7/2012 | Saracen | A61B 6/4458 901/29 |
| 2014/0044141 | A1 | 2/2014 | Bouliniere | |
| 2018/0140262 | A1* | 5/2018 | Hertzoff | A61B 6/08 |

FOREIGN PATENT DOCUMENTS

| | | |
|---|---|---|
| CN | 106552322 A | 4/2017 |
| CN | 106975162 A | 7/2017 |
| EP | 2921206 A1 | 9/2015 |
| EP | 3136400 A1 | 3/2017 |

OTHER PUBLICATIONS

Lucian Wielopolski et al., Patient Positioning in Static Beams for Boron Neutron Capture Therapy of Malignant Glioma, Radiation Medicine: vol. 18, No. 6, 381-387, p. 2000.
Current status of neutron capture therapy, IAEA-TECDOC-1223, International Atomic Energy Agency, 2001.

* cited by examiner

NEUTRON CAPTURE THERAPY SYSTEM

CROSS-REFERENCE TO RELATED PATENT APPLICATION

This application is a continuation application of International Application No. PCT/CN2018/100987, filed on Aug. 17, 2018, which claims priority to Chinese Patent Application No. 201711365076.4, filed on Dec. 18, 2017, and Chinese Patent Application No. 201721777784.4, filed on Dec. 18, 2017, the disclosures of which are hereby incorporated by reference.

FIELD

The present disclosure relates to a radioactive irradiation system, and more particularly to a neutron capture therapy system.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

As atomics moves ahead, radiotherapy such as Cobalt-60 therapy, linear accelerator therapy and electron beam therapy has been one of the major approaches to cancer treatment. However, conventional photon or electron therapy has been undergone physical restrictions of radioactive rays. For example, a large amount of normal tissues on a beam path will be damaged as tumor cells are killed. Moreover, tumor cells have different radiosensitivity, and as a result conventional radiotherapy falls short of treatment effectiveness on radioresistant malignant tumors (such as glioblastoma multiforme and melanoma).

To reduce radiation-induced damage to the normal tissue around the tumor, targeted therapy in chemotherapy has been applied to radiotherapy. For high-radioresistant tumor cells, proton therapy, heavy particle therapy, neutron capture therapy, and the like using a radiation source with high relative biological effectiveness (RBE) are being actively developed at present. The neutron capture therapy combines the target therapy with the RBE. For example, the boron neutron capture therapy (BNCT). By virtue of specific grouping of boron-containing drugs in the tumor cells and precise neutron beam irradiation to provide a better cancer treatment option than conventional radiotherapy.

To implement precise neutron beam irradiation, in a preparation room, it is necessary to precisely position and mark the tumor position of a patient through CT imaging and the like and a laser positioning system. In an irradiation room, it is necessary to position the patient through the laser positioning system and the mark made in the preparation room to enable a neutron beam to aim the tumor for irradiation. A conventional laser positioning system includes four laser emitters fixedly installed on the walls and ceilings of the preparation room and the irradiation room, respectively. Because the laser emitters are fixed, when an infusion tube, a treatment bed, and other objects in the preparation room and/or the irradiation room block a laser beam, it is difficult to implement precise positioning of the patient, and as a result precise neutron beam radiotherapy cannot be implemented.

SUMMARY

To resolve the foregoing problem, one aspect of the present disclosure provides a neutron capture therapy system. The neutron capture therapy system includes an irradiation room configured to irradiate an irradiated body with a neutron beam, a preparation room configured to implement preparation work required to irradiate the irradiated body with the neutron beam, and an auxiliary positioner disposed in the irradiation room and/or the preparation room. The irradiation room includes a first shielding wall and a collimator disposed on the first shielding wall for emitting the neutron beam, and wherein the neutron beam is emitted from the collimator and defines a neutron beam axis. The auxiliary positioner includes a laser emitter for emitting a laser beam to position the irradiated body, and wherein a position of the laser emitter is selectable.

Compared with the prior art, the technical solution recorded in this embodiment has the following beneficial effects: The position of the laser emitter is selectable. Therefore, the irradiated body can be positioned in any case to implement precise irradiation.

Preferably, the auxiliary positioner includes a base and a cantilever extending perpendicularly from the base, and the laser emitter is disposed on the cantilever.

Further, the cantilever is provided with a guiderail for guiding the laser emitter to move and a positioning member for fixing the laser emitter at a predetermined position.

Preferably, the cantilever is telescopic.

Preferably, a plurality of laser emitters are disposed, and a plurality of laser emitters are sequentially arranged from a position close to an end, away from the base, of the cantilever.

Preferably, the preparation room includes a first wall provided with a collimator model having a same structure and size as the collimator, and the auxiliary positioner is disposed around the collimator and/or the collimator model and installed on the first shielding wall and/or the first wall.

Preferably, the preparation room includes a first wall provided with a collimator model having a same structure and size as the collimator, and the auxiliary positioner is installed on the collimator and/or the collimator model.

Preferably, the neutron capture therapy system further comprising a neutron beam generating unit for generating the neutron beam, wherein the neutron beam generating unit includes an accelerator configured to accelerate a charged particle beam, a neutron beam generator reacting with the charged particle beam to generate the neutron beam, and a charged particle beam transmitter located between the accelerator and the neutron beam generator and configured to transmit the charged particle beam.

Preferably, the base and the cantilever are both rectangular cuboids, the first shielding wall and the first wall are respectively provided with a fixing portion and a positioning portion which are respectively disposed around the collimator and the collimator model and adapted to fix the auxiliary positioner, wherein the neutron capture therapy system defines XYZ coordinates including a Y-axis parallel to the neutron beam axis, a Z-axis perpendicular to a ground, and an X-axis orthogonal to the Y-axis and the Z-axis, the fixing portion includes a first fixing portion located right above the collimator and arranged in parallel to the X-axis, a second fixing portion located on a left side of the collimator and arranged in parallel to the Z-axis, and a third fixing portion located on a right side of the collimator and arranged parallel to the Z-axis direction, the positioning portion includes a first positioning portion, a second positioning portion, and a third positioning portion respectively disposed corresponding to the first fixing portion, the second fixing portion, and the third fixing portion, the structures and sizes of the first fixing portion, the second fixing portion, and the third fixing portion are respectively the same as those of the first positioning portion, the second positioning portion, and the third positioning portion, when a center of a projection of the collimator on the first shielding wall and a center of a projection of the collimator model on the first wall are respectively as adapted to be reference points, coordinate values of a center of the first fixing portion, the second fixing portion and the third fixing portion are respectively the same as coordinate values of a center of the first positioning portion, the second positioning portion and the third positioning portion.

Preferably, the base is a hollow cylinder, the cantilever is a hexahedron disposed perpendicular to the base, the first shielding wall and the first wall are respectively provided with a fixing portion and a positioning portion for fixing the auxiliary positioner, wherein the neutron capture therapy system defines XYZ coordinates including a Y-axis parallel to the neutron beam axis, a Z-axis perpendicular to a ground, and an X-axis orthogonal to the Y-axis and the Z-axis, and the fixing portion and the positioning portion are hollow circular rings having an identical size and a center of a circle respectively the same as a center of a projection of the collimator on the first shielding wall and a center of a projection of the collimator model on the first wall.

Preferably, the base is provided with an annular track on which the cantilever slides in a circumferential direction and a fastening member for fixing the cantilever at a predetermined position, and the cantilever is provided with a guiding portion fitting with the annular track and a clamping member fitting with the fastening member to fix the cantilever.

Preferably, the base is detachably mounted on the first shielding wall and/or the first wall.

Preferably, the base is detachably mounted on the collimator and/or the collimator model.

In another aspect of the present disclosure provides neutron capture therapy system, the neutron capture therapy system includes a irradiation room provided with a collimator for a neutron beam to be emitted, a preparation room provided with a collimator model having a same structure and size as the collimator, and an auxiliary positioner disposed in the irradiation room and/or the preparation room, wherein the auxiliary positioner includes a base and a cantilever extending from the base. The cantilever is provided with at least one laser emitter for emitting a laser beam. A position of the laser emitter is selectable, and a relative position between the laser emitter and the collimator is correspond to a relative position between the laser emitter and the collimator model.

Preferably, the base is detachably mounted to the irradiation room and/or the preparation room.

In yet another aspect of the present disclosure provides neutron capture therapy system, the neutron capture therapy system includes a irradiation room configured to irradiate an irradiated body with a neutron beam, and an auxiliary positioner disposed in the irradiation room, wherein the auxiliary positioner includes a cantilever provided with at least one laser emitter for emitting a laser beam to position the irradiated body. A position of the laser emitter is selectable.

Preferably, the auxiliary positioner further includes a base from which the cantilever extends perpendicularly, and wherein the laser emitter is disposed on the cantilever.

Preferably, the base is detachably mounted on the irradiation room.

Preferably, a collimator is disposed on the irradiation room, the auxiliary positioner is detachably mounted on the collimator.

BRIEF DESCRIPTION OF THE DRAWINGS

The accompanying drawings illustrate one or more embodiments of the disclosure and together with the written description, serve to explain the principles of the disclosure. Wherever possible, the same reference numbers are used throughout the drawings to refer to the same or like elements of an embodiment.

DETAILED DESCRIPTION OF THE DISCLOSURE

The embodiments of the present disclosure are further described in detail below with reference to the accompanying drawings, so that those skilled in the art can implement the technical solutions according to the description.

Neutron capture therapy has been increasingly practiced as an effective approach for treating cancer in recent years, and BNCT is the most common. Neutrons for BNCT may be supplied by a nuclear reactors, a D-T neutron generators, a D-D neutron generators, a spallation neutron sources or accelerators. Take accelerator-based BNCT for example in the embodiments of the present disclosure. Basic components for the accelerator-based BNCT generally include an accelerator configured to accelerate a charged particles (such as protons and deuterons, etc.), a neutron generator, a heat removal system, and a beam shaping assembly. The accelerated charged particles react with a metal neutron generator to generate neutrons. Suitable nuclear reactions are selected according to characteristics such as the desired neutron yield and energy, the energy and the current of the accelerated charged particle, and materialization of the metal neutron generator. The most discussed nuclear reactions are $^7Li(p,n)^7Be$ and $^9Be(p,n)^9B$.

Figure 1:
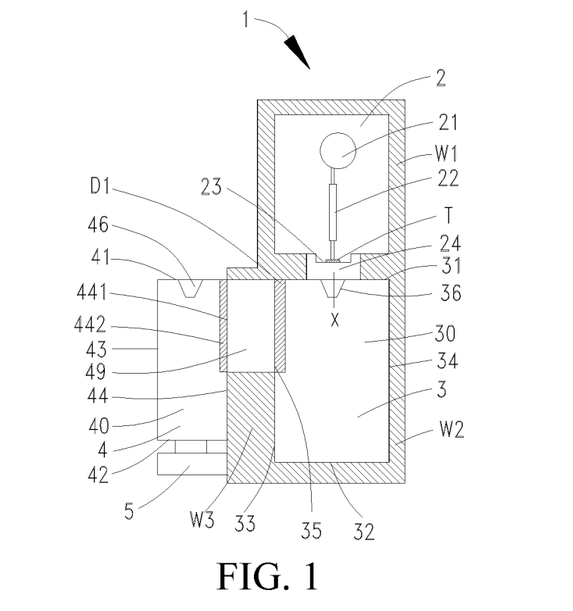
FIG. 1 is a top view of a neutron capture therapy system according to the present disclosure.

As shown in FIG. 1, a neutron capture therapy system 1 includes a neutron beam generating unit 2 configured to generate a therapeutic neutron beam, an irradiation room 3 configured to irradiate an irradiated body, for example, a patient, with the neutron beam, a preparation room 4 configured to perform preparation work before irradiation, a management room 5 configured to implement irradiation control, and an auxiliary positioner 6 configured to auxiliary positioning of the patient in special occasions.

The neutron beam generating unit 2 is configured to generate the neutron beam outside the irradiation room 3 and irradiate the patient with the neutron beam. The neutron beam generating unit 2 includes a cyclotron 21 configured to accelerate a charged particle beam, a neutron beam generator 23 that reacts with the charged particle beam to generate the neutron beam, and a charged particle beam transmitter 22 located between the cyclotron 21 and the neutron beam generator 23 and configured to transmit the charged particle beam. The neutron beam generating unit 2 is surrounded by a shielding wall W1 made of concrete. The charged particle beam transmitter 22 transmits the charged particle beam to the neutron beam generator 23, one end of the charged particle beam transmitter 22 is connected to the cyclotron 21, and the other end of the charged particle beam transmitter 22 is connected to the neutron beam generator 23. In other embodiments, other accelerators may be used in place of the cyclotron. A beam control device such as a beam adjuster, a current monitor, and a charged particle scanner may be disposed on the charged particle beam transmitter 22 according to an actual requirement. The beam control device controls a direction of travel and a beam diameter of the charged particle beam. The current monitor measures a current value (that is, charge, and a radiation dose rate) of the charged particle beam in real time. The charged particle scanner scans the charged particle beam and controls an irradiation position of the charged particle beam with respect to the neutron beam generator 23. The neutron beam generator 23 includes a target T that reacts with the charged particle beam to generate a neutron beam and a beam shaping assembly 24 that slows down and shields against the generated neutron beam. The neutron beam generated in the neutron beam generator 23 includes a high-speed neutron beam, an epithermal neutron beam, a thermal neutron beam, and a gamma ray. Specifically, the beam shaping assembly 24 includes a moderator that can slow down the neutron beam generated from the target T to an epithermal neutron energy range, a reflector that guides neutrons that deviate from a determined route back to the moderator to increase the intensity of the epithermal neutron beam, a thermal neutron absorber configured to absorb thermal neutrons to protect superficial a normal tissue from an overdose during treatment, and a radiation shield configured to shield against leaked neutrons and photons to reduce a dose to the normal tissue in a non-irradiation area. In one embodiment, the target T is made of lithium metal, the charged particle beam is accelerated enough to overcome the energy of the coulomb repulsion of atomic nuclei of the target T, and the $^7Li(p,n)^7Be$ nuclear reaction occurs between the charged particle beam and the target T to generate the neutron beam. The nuclear reaction mainly occurs between the epithermal neutron beam and boron that enters a tumor in the body of the patient to exert a therapeutic effect. The target T is disposed outside the shielding wall W1, and the beam shaping assembly 24 is buried in the shielding wall W1 along a traveling direction of the neutron beam.

Figure 2:
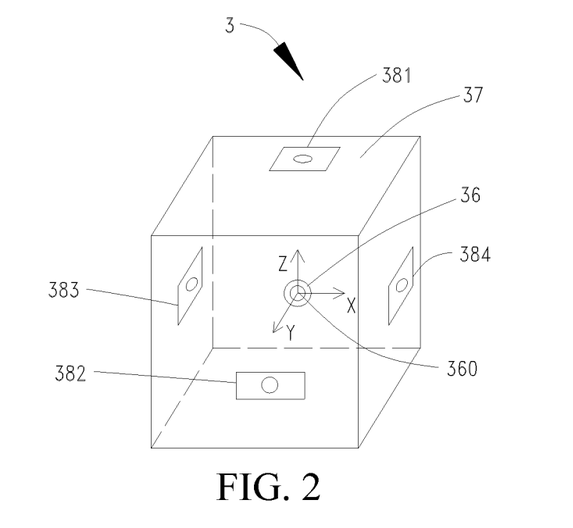
FIG. 2 is a schematic diagram of an irradiation room installed with a positioning device in FIG. 1.

Referring to FIG. 2, the irradiation room 3 includes a shielding wall W2, a ceiling 37, a doorway 35 opened in the shielding wall W2 for a patient to enter or exit, a shielding door D1 for opening and closing the doorway 35, and a shielded space 30 surrounded by the shielding wall W2, the ceiling 37, and the shielding door D1. The patient is placed in the shielded space 30 to receive treatment of neutron beam irradiation. The shielding wall W2 includes a first shielding wall 31 adjacent to the beam shaping assembly 24, a second shielding wall 32 opposite to the first shielding wall 31, and a third shielding wall 33 and a fourth shielding wall 34 connected between the first shielding wall 31 and the second shielding wall 32 and disposed opposite to each other. A conical collimator 36 is disposed on the first shielding wall 31 for emitting the neutron beam. The neutron beam is emitted from the collimator 36 and defines a neutron beam axis X. In other embodiments, the collimator 36 may be disposed into another shape such as a cylinder, a cuboid and other shapes. The third shielding wall 33 is located on a left side of the collimator 36, and the doorway 35 is formed through the third shielding wall 33 in a direction perpendicular to the neutron beam axis X. A fixing portion 39 for fixing the auxiliary positioner 6 to the first shielding wall 31 is disposed in the first shielding wall 31, and the fixing portion 39 is disposed around the collimator 36.

Figure 3:
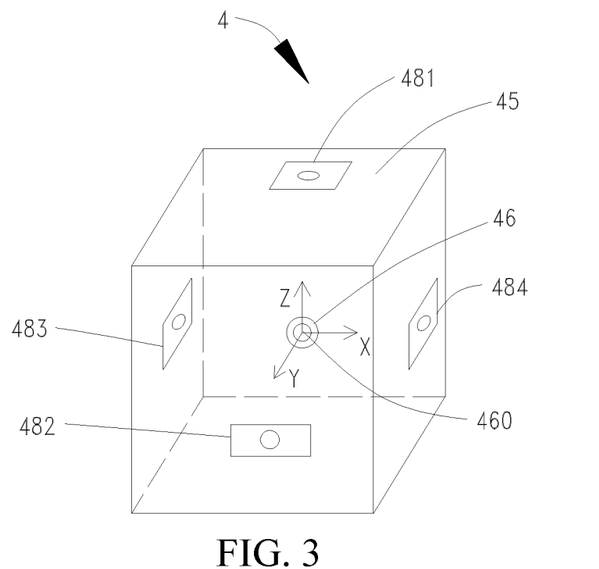
FIG. 3 is a schematic diagram of a preparation room installed with a positioning module in FIG. 1.

Referring to FIG. 3, the preparation room 4 is a room configured to implement preparation work required before irradiating the patient S with the neutron beam N. The preparation work includes fixing the patient to a treatment table, positioning the tumor of the patient, and completing three-dimensional positioning marks. In this embodiment of the present disclosure, the preparation room 4 is disposed on a left side of the irradiation room 3, and the preparation room 4 and the irradiation room 3 are separated by the shielding wall W3. In other embodiments, the preparation room 4 may be disposed at any orientation of the irradiation room 3. The preparation room 4 includes a first wall 41 disposed parallel to the first shielding wall 31, a second wall 42 located opposite to the first wall 41, a third wall 43 and a fourth wall 44 that are located at two ends of the first wall 41 and the second wall 42 and connect the first wall 41 and the second wall 42, respectively, and a top wall 45 located above the first wall 41, the second wall 42, the third wall 43, and the fourth wall 44. The first wall 41 is provided a collimator model 46 having a same structure and size as the collimator 36 in the irradiation room 3. The collimator model 46 may be alternatively installed in any wall of the second wall 42, the third wall 43, and the fourth wall 44 of the preparation room 4. The fourth wall 44 is provided with an entrance 441 formed through the fourth wall 44 in the direction perpendicular to the neutron beam axis X for the patient to enter and exit and a door 442 for opening or closing the entrance 441. A passage 49 is provided between the entrance 441 of the preparation room 4 and the doorway 35 of the irradiation room 3 for the patient to enter the irradiation room 3 from the preparation room 4. The first wall 41, the second wall 42, the third wall 43, the fourth wall 44, the top wall 45, and the door 442 surround a closed space 40, and the patient S undergoes the preparation work before irradiation in the closed space 40. In this embodiment, the first wall 41, the second wall 42, the third wall 43, the fourth wall 44 and the top wall 45 of the preparation room 4 are normal walls, the space 40 is an unshielded space. In other embodiments, the first wall 41, the second wall 42, the third wall 43, the fourth wall 44 and the top wall 45 of the preparation room 4 are shielded walls, and the space 40 is a shielded space. The first wall 41 is also provided with a positioning portion 49 for fixing the auxiliary positioner 6 to the first wall 41, and the positioning portion 49 is disposed around the collimator model 46. The structure and size of the positioning portion 49 are identical with those of the fixing portion 39 in the irradiation room 3. Moreover, when a center 360 of the projection of the collimator 36 on the first shielding wall 31 and a center 460 of the projection of the collimator model 46 on the first wall 41 are respectively used as reference points, the center 360 and the center 460 are centers of circle in this embodiment, and which is referred to as a collimator center 360 and a collimator model center 460, respectively. In this case, a coordinate values of a center of the fixing portion 39 is the same as a coordinate values of a center of the positioning portion 49. Specifically, the neutron capture therapy system defines XYZ coordinates including a Y-axis parallel to the neutron beam axis X, a Z-axis perpendicular to a ground, and an X-axis orthogonal to the Y-axis and the Z-axis.

The management room 5 is a room configured to manage the entire procedure implemented using the neutron capture therapy system 1. For example, a manager visually confirms the condition of the preparation work in the preparation room 4 from inside of the management room 5, the manager operates the control device to control the start and stop of the irradiation of a neutron beam, and the like.

Referring to FIG. 1 and FIG. 2, to position and precisely irradiate the tumor of the patient S, a positioning system is disposed in both the irradiation room 3 and the preparation room 4. Specifically, the second shielding wall 32, the third shielding wall 33, the fourth shielding wall 34, and the ceiling 37 of the irradiation room 3 are respectively provided with positioning devices for positioning of the patient S. The positioning device includes a first laser positioner 381 disposed on the ceiling 37 and located above the collimator 36, a second laser positioner 382 disposed on the second shielding wall 32 and located in front of the collimator 36, a third laser positioner 383 disposed on the third shielding wall 33 and located on the left side of the collimator 36, and a fourth laser positioner 384 disposed on the fourth shielding wall 34 and located on a right side of the collimator 36. The positions of the first laser positioner 381, the second laser positioner 382, the third laser positioner 383, and the fourth laser positioner 384 are fixed, that is, the laser beams respectively emitted by the first laser positioner 381, the second laser positioner 382, the third laser positioner 383, and the fourth laser positioner 384 for positioning the patient are uniquely determined in a three-dimensional space.

Referring to FIG. 1 and FIG. 3, the second wall 42, the third wall 43, the fourth wall 44, and the top wall 45 of the preparation room 4 are respectively provided with a positioning module for positioning and marking the tumor of the patient S. The positioning module includes a first positioner 481 disposed on the top wall 45 and located above the collimator model 46, a second positioner 482 disposed on the second wall 42 and located in front of the collimator model 46, a third positioner 483 disposed on the third wall 43 and located on the left side of the collimator model 46, and a fourth positioner 484 disposed on the fourth wall 44 and located on the right side of the collimator model 46. The positions of the first positioner 481, the second positioner 482, the third positioner 483, and the fourth positioner 484 are fixed, that is, the laser beams respectively emitted by the first positioner 481, the second positioner 482, the third positioner 483, and the fourth positioner 484 for positioning the patient are uniquely determined in a three-dimensional space.

The position relationships between the first positioner 481, the second positioner 482, the third positioner 483, and the fourth positioner 484 and the collimator model 46 are respectively correspondingly the same as those between the first laser positioner 381, the second laser positioner 382, the third laser positioner 383, and the fourth laser positioner 384 and the collimator 36. Specifically, taking the collimator center 360 and the collimator model center 460 as the reference points, respectively, the coordinate values of the first laser positioner 381, the second laser positioner 382, the third laser positioner 383, and the fourth laser positioner 384 are respectively correspondingly the same as those of the first positioner 481, the second positioner 482, the third positioner 483, and the fourth positioner 484.

In the preparation room 4, the CT imaging combined with the positioning module is used to position the tumor of the patient and make three-dimensional marks on the patient's body surface, and then the patient S is sent in the irradiation room 3 through the passage 49. After the patient enters the irradiation room 3, the patient is positioned by the positioning device in the irradiation room 3 and the three-dimensional marks prepared in advance on the body surface of the patient, so that a neutron beam aims at the tumor for irradiation. Specific marking methods and positioning methods are techniques well known to a person of ordinary skill in the art, details are not described herein.

Figure 4:
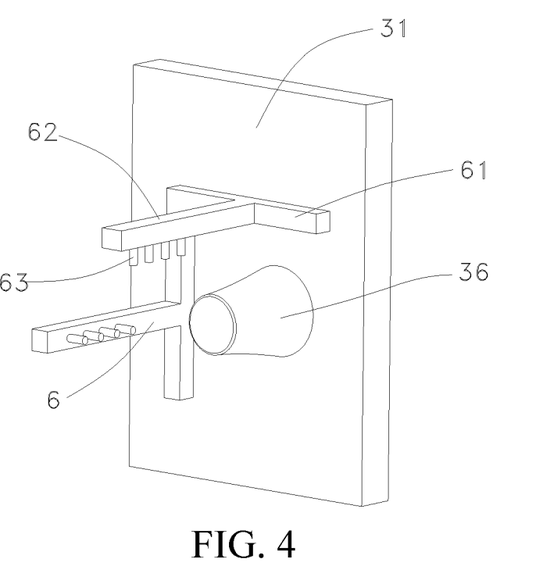
FIG. 4 is a perspective view of an auxiliary positioner according to first embodiment of the present disclosure.
Figure 5:
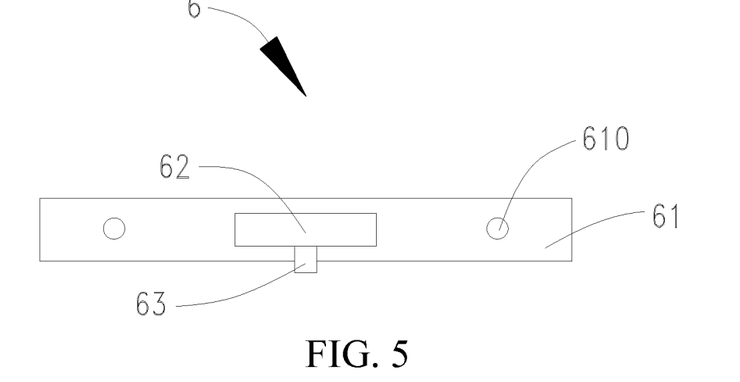
FIG. 5 is a front view of the auxiliary positioner in FIG. 4.

As shown in FIG. 4 and FIG. 5, the auxiliary positioner 6 of a first embodiment of the present disclosure includes a base 61 installed on the fixing portion 39 of the irradiation room 3 or the positioning portion 49 of the preparation room 4, a cantilever 62 disposed perpendicular to the base 61, and four laser emitters 63 fixedly installed on the cantilever 62. The base 61 and the cantilever 62 are both rectangular cuboids, the cantilever 62 extends perpendicularly from a central position of the base 61, and the laser emitters 63 is installed on a plane of the cantilever 62 facing the collimator 36 or the collimator model 46. As observed in the X-axis direction, in the Y-axis direction, a size of the cantilever 62 is greater than a size of the collimator 36 and a size of the collimator model 46. The laser emitters 63 are all located outside the collimator 36 and the collimator model 46. The base 61 is provided with at least two positioning holes 610 penetrating the base 61 along the Y-axis direction to fix the base 61 to the first shielding wall 31 or the first wall 41. The base 61 and the cantilever 62 are made of metal or plastic with low activity, and are integrally formed. The laser emitters 63 are sequentially arranged along the Y-axis direction at equal intervals from a position close to an end of the cantilever 62 away from the base 61. Because the auxiliary positioner 6 has a plurality of laser emitters 63, when one or more laser beams are blocked by an obstacle, another unblocked laser beams can be flexibly selected for positioning, thereby implementing precise positioning and precise irradiation.

In other embodiments, the base 61 and the cantilever 62 may be separately formed and then assembled. The base 61 and the cantilever 6 are not limited to rectangular cuboids, but may be other shapes such as hexagonal prisms. A quantity of the laser emitters 63 is any quantity greater than 1.

In other embodiments, the laser emitter 63 may be disposed to be movable along the Y-axis direction, correspondingly, the cantilever 62 is provided with a guiderail for guiding the laser emitters 63 and a positioning member for fixing the laser emitters 63 at a predetermined position. In another embodiment, the cantilever 62 can be configured as a telescopic structure, and the position of the laser emitters 63 on the Y-axis direction can be adjusted by extending or retracting the cantilever 62. In these two embodiments, because the position of the laser emitters 63 on the Y-axis direction is adjustable, only one laser emitter 63 is needed to implement precise positioning and precise irradiation, and at the same time manufacturing costs are reduced.

Figure 7:
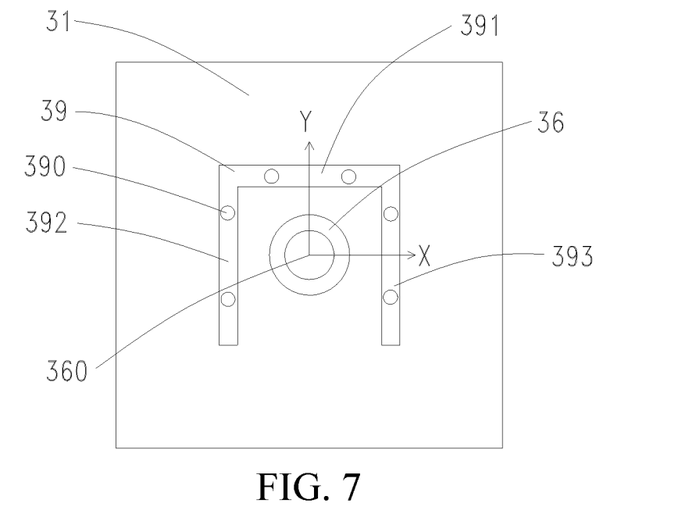
FIG. 7 is a schematic diagram of a fixing portion corresponding to the auxiliary positioner in first embodiment in an irradiation room.

As shown in FIG. 7, as observed in the Y-axis direction, the fixing portion 39 and the positioning portion 49 corresponding to the auxiliary positioner 6 in the first embodiment are two "Π"-shaped structure with the collimator center 360 and the collimator model center 460 as the centers, respectively. Specifically, the fixing portion 39 includes a first fixing portion 391 located right above the collimator 36 and arranged parallel to the X-axis direction, a second fixing portion 392 located on the left side of the collimator 36 and arranged parallel to the Z-axis direction, and a third fixing portion 393 located on the right side of the collimator 36 and arranged parallel to the Z-axis direction. The first fixing portion 391, the second fixing portion 392, and the third fixing portion 393 are buried in the first shielding wall 31. As observed in the Y-axis direction, the first fixing portion 391, the second fixing portion 392, and the third fixing portion 393 are three rectangles connected head to tail, and the first fixing portion 391, the second fixing portion 392, and the third fixing portion 393 form a "Π" shape disposed around the collimator center 360. The first fixing portion 391, the second fixing portion 392, and the third fixing portion 393 are respectively provided with at least two fixing holes 390 for fixing the base 61. The fixing holes 390 and the positioning holes 610 of the base 61 are threaded holes, the base 61 is fixed on the first fixing portion 391, the second fixing portion 392, and the third fixing portion 393 via screws to form a detachable fixed connection. In other embodiments, the base 61 and the first fixing portion 391, the second fixing portion 392, and the third fixing portion 393 may be fixed together in a manner such as a snap-fit through a groove and a protrusion or magnetic attraction to form a detachable fixed connection.

Figure 8:
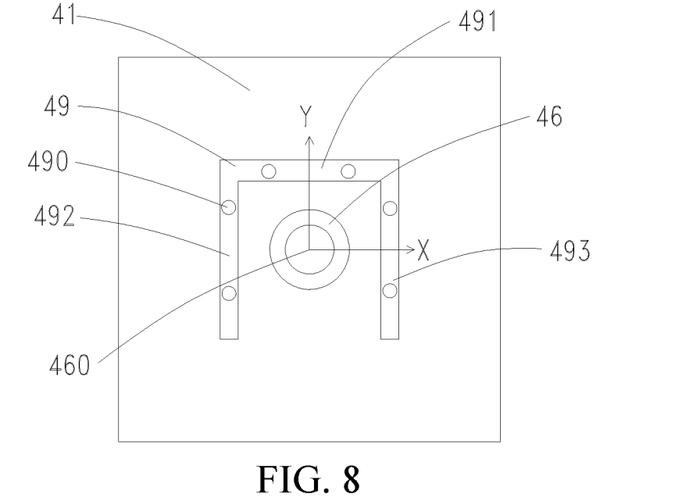
FIG. 8 is a schematic diagram of a positioning portion corresponding to the auxiliary positioner in first embodiment in a preparation room.

As shown in FIG. 8, the positioning portion 49 includes a first positioning portion 491, a second positioning portion 492, and a third positioning portion 493 and at least two fixing holes 490 respectively provided in the first positioning portion 491, the second positioning portion 492, and the third positioning portion 493 for fixing the base 61. Because the fixing portion 39 and the positioning portion 49 have correspondingly the same structure, size, and coordinate values of centers when the collimator center 360 and the collimator model center 460 are respectively used as reference points, only the fixing portion 39 is described in detail herein. For the structure of the positioning portion 49 and the position relationship between the positioning portion 49 and the collimator model 46, refer to the foregoing description of the structure and size of the fixing portion 39 and the position relationship between the positioning portion 49 and the collimator 36.

One or more auxiliary positioners 6 can be installed on the first fixing portion 391, the second fixing portion 392, the third fixing portion 393, the first positioning portion 491, the second positioning portion 492, or the third positioning portion 493 to replace one or more laser emitters of the first laser positioner 381, the third laser positioner 383, and the fourth laser positioner 384 in the irradiation room 3 and the first positioner 481, the third positioner 483, and the fourth positioner 484 in the preparation room 4 to position the irradiated body.

In other embodiments, the fixing portion 39 and the positioning portion 49 may be disposed on the collimator 36, the collimator model 46 or other wall surfaces of the irradiation room 3 and the preparation room 4, respectively. Correspondingly, precise positioning can be similarly implemented by adjusting the structure of the auxiliary positioner 6.

Figure 6:
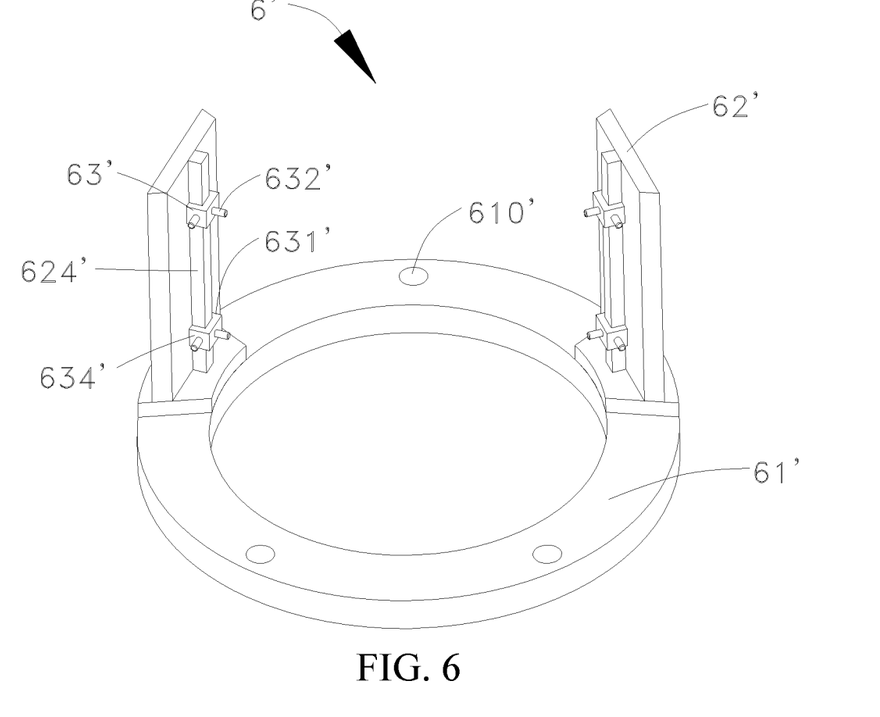
FIG. 6 is a perspective view of an auxiliary positioner according to second embodiment of the present disclosure.

As shown in FIG. 6, an auxiliary positioner 6' of a second embodiment of the present disclosure includes a base 61' installed on a fixing portion 39' or a positioning portion 49', a cantilever 62' installed on the base 61', and a laser emitting device 63' installed on the cantilever 62'. The cantilever 62' is provided with a guiderail 624' for guiding the laser emitting device 63' to move along the Y-axis direction. The laser emitting device 63' includes a sliding member 631' that can slide on the guiderail 624', a laser emitters 632' installed on the sliding member 631', and a locking member 634' that fixes the sliding member 631' on the guiderail 624'. The base 61' is a hollow cylinder, the cantilever 62' is a hexahedron having an isosceles trapezoidal cross section in a direction perpendicular to the Y-axis direction, and the laser emitters 63' are installed on the guiderail 624' of the cantilever 62' facing the collimator 36 or the collimator model 46. The guiderail 624' is a rectangular cuboid parallel to the Y-axis direction, and the sliding member 631' spans the guiderail 624'. The locking member 634' selectively locks the sliding member 631' at a position of the guiderail 624'. The base 61' is provided with at least two positioning holes 610' for fixing the base 61' to the first shielding wall 31 and the first wall 41. In the Y-axis direction, the size of the cantilever 62' is greater than the sizes of the collimator 36 and the collimator model 46. That is, the cantilever 62' protrudes from the collimator 36 and the collimator model 46. The laser emitters 63' are all located outside the collimator 36 and the collimator model 46. The bases 61' is provided with an annular track (not shown) for the cantilever 62' to slide in a circumferential direction and a fastening member (not shown) for fixing the cantilever 62' at a predetermined position. Correspondingly, the cantilever 62' is provided with a guiding portion (not shown) fitting with the annular track and a clamping member (not shown) fitting with the fastening member to fix the cantilever 62'. The guiderail and a guiding member are common forms such as a fit of a groove and a protrusion, and the fastening member and the clamping member are common locking devices, for example, a fit of an elastic body and a groove, and a fit of a bolt and a threaded hole. The bases 61' and the cantilever 62' are made of metal or plastic with low activity. In this embodiment, two cantilevers 62' are installed on the bases 61', and two laser emitting devices 63' are disposed on each cantilever 62'. According to actual requirement, one to three cantilever 62' may be installed on the bases 61', and the quantity of the laser emitting devices 63' is greater than or equal to 1. Because the laser emitters 63' may move along the guiderail 624' in the Y-axis direction and may be positioned at any predetermined position, when an obstacle blocks a laser beam, the position of the laser emitting device 63' may be flexibly adjusted until the laser beam is not blocked, thereby implementing precise positioning and precise irradiation.

In other embodiments, a plurality of laser emitting devices 63' may be disposed, and the plurality of laser emitting devices 63' are sequentially arranged in the Y-axis direction at equal intervals from a position close to an end, away from the base 61', of the cantilever 62' and are fixedly installed. Because a plurality of laser emitting devices 63' are disposed, when an obstacle blocks one or more of the laser beams, another unblocked laser beam may be flexibly selected to perform positioning, thereby implementing precise positioning and precise irradiation. The cantilevers 62' may be disposed to be fixedly installed on the bases 61'. The cantilevers 62' may be disposed to be telescopic, and the telescopic cantilevers 62' are adjusted to adjust the positions of the laser emitters 63' in the Y-axis direction. Because the position of the laser emitting device 63' in the Y-axis direction is adjustable, only one laser emitting device 63' needs to be disposed to implement precise positioning and precise irradiation, and at the same time manufacturing costs are reduced.

Figure 9:
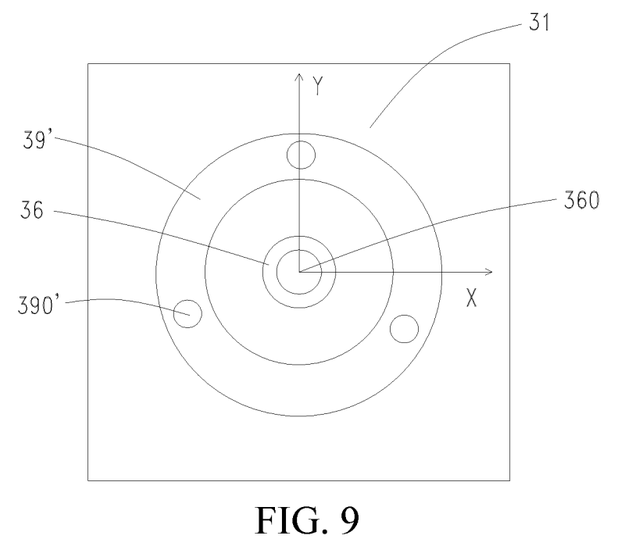
FIG. 9 is a schematic diagram of a fixing portion corresponding to the auxiliary positioner in second embodiment in an irradiation room.
Figure 10:
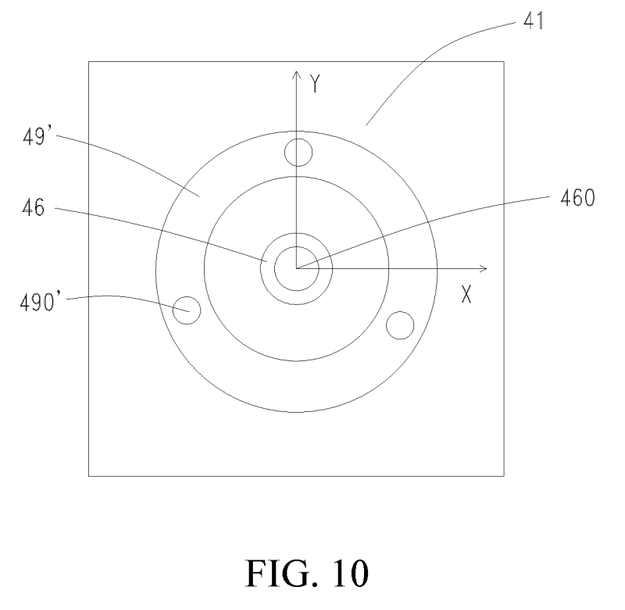
FIG. 10 is a schematic diagram of a positioning portion corresponding to the auxiliary positioner in second embodiment in a preparation room.

As shown in FIG. 9 and FIG. 10, as observed in the Y-axis direction, the fixing portion 39' and the positioning portion 49' corresponding to the auxiliary positioner 6' in the second embodiment are two circular rings with the collimator center 360 and the collimator model center 460 as the centers, respectively. The fixing portion 39' and the positioning portion 49' has the same size, and respectively surround the collimator 36 and the collimator model 46 and are buried in the first shielding wall 31 and the first wall 41, respectively. The fixing portion 39' and the positioning portion 49' are respectively provided with at least two fixing holes 390', 490' for fixing the base 61'. The fixing holes 390', 490' and the positioning holes 610' are threaded holes. The base 61' is fixed to the fixing portion 39' and the positioning portion 49' via screws to form a detachable fixed connection. In other embodiments, the bases 61' may be fixed together with the fixing portion 39' and the positioning portion 49' in a manner such as a fastening fit of a groove and a protrusion or magnetic attraction to form a detachable fixed connection.

One or more cantilevers 62' on the auxiliary positioner 6' may be positioned at corresponding positions to replace one or more laser emitters of the first laser positioner 381, third laser positioner 383, and fourth laser positioner 384 in the irradiation room 3 and the first positioner 481, the third positioner 483, and the fourth positioner 484 of the preparation room 4 to position the irradiated body.

In other embodiments, the fixing portion 39' and the positioning portion 49' may be disposed on the collimator 36, the collimator model 46 or other wall surfaces of the irradiation room 3 and the preparation room 4, respectively. Correspondingly, precise positioning can be similarly implemented by adaptively adjusting the structure of the auxiliary positioner 6'.

The auxiliary positioner 6, 6' can be used to replace any one or more laser positioners of the first laser positioner 381, the third laser positioner 383, and the fourth laser positioner 384 in the irradiation room 3 and the first positioned 481, the third positioned 483, and the fourth positioned 484 in the preparation room 4 to position the patient, and the quantity of laser positioners that need to be replaced is determined according to an actual case. In actual application, in the preparation room 4 and the irradiation room 3, when a light beam emitted by one or more laser positioners fixed installed on the wall and ceiling is blocked and positioning cannot be implemented, the auxiliary positioner 6, 6' is installed at the corresponding fixing portions 39, 39' and positioning portion 49, 49' to replace the one or more laser positioners to implement positioning. A same group of auxiliary positioners 6, 6' may be used in the preparation room 4 and the irradiation room 3. That is, after the tumor of the patient S is positioned and marked in the preparation room 4, the one or more auxiliary positioners 6, 6' are detached and installed in the irradiation room 3 for subsequent use. Alternatively, a required quantity of auxiliary positioners 6, 6' may be installed in both the preparation room 4 and the irradiation room 3, and it is not necessary to detach the auxiliary positioner 6, 6' in the preparation room 4 for reuse in the irradiation room 3.

The neutron capture therapy system disclosed in the present disclosure is not limited to the content in the foregoing embodiments and the structures represented in the accompanying drawings. All obvious changes, replacements or modifications made to the materials, shapes, and positions of the members based on the present disclosure fall within the protection scope of the present disclosure.

Although the illustrative embodiments of the present invention have been described above in order to enable those skilled in the art to understand the present invention, it should be understood that the present invention is not to be limited the scope of the embodiments. For those skilled in the art, as long as various changes are within the spirit and scope as defined in the present invention and the appended claims, these changes are obvious and within the scope of protection claimed by the present invention.

What is claimed is:

1. A neutron capture therapy system, comprising:
   an irradiation room configured to irradiate an irradiated body with a neutron beam, wherein the irradiation room comprises a first shielding wall and a collimator disposed on the first shielding wall for emitting the neutron beam, and wherein the neutron beam is emitted from the collimator and defines a neutron beam axis,
   a preparation room configured to implement preparation work required to irradiate the irradiated body with the neutron beam, wherein the preparation room comprises a first wall provided with a collimator model corresponding to the collimator, and
   a first auxiliary positioner disposed in the irradiation room and a second auxiliary positioner disposed in the preparation room, wherein each of the first auxiliary positioner and the second auxiliary positioner comprises a laser emitter for emitting a laser beam to position the irradiated body, the first auxiliary positioner is detachably mounted on the first shielding wall or the collimator, the second auxiliary positioner is detachably mounted on the first wall or the collimator model, and wherein a position of the laser emitter is selectable.

2. The neutron capture therapy system according to claim 1, wherein each of the first auxiliary positioner and the second auxiliary positioner comprises a base and a cantilever extending perpendicularly from the base, and the laser emitter is disposed on the cantilever.

3. The neutron capture therapy system according to claim 2, wherein the cantilever is provided with a guiderail for guiding the laser emitter to move and a positioning member for fixing the laser emitter at a predetermined position.

4. The neutron capture therapy system according to claim 2, wherein the cantilever is telescopic.

5. The neutron capture therapy system according to claim 2, wherein a plurality of laser emitters are disposed on the cantilever, the cantilever has an end located away from the base, and the plurality of laser emitters are sequentially arranged at intervals from a position close to the end of the cantilever being located away from the base.

6. The neutron capture therapy system according to claim 2, wherein the first auxiliary positioner is disposed around the collimator and installed on the first shielding wall, and the second auxiliary positioner is disposed around the collimator model and installed on the first wall.

7. The neutron capture therapy system according to claim 1, wherein the first auxiliary positioner is installed on the collimator, and the second auxiliary positioner is installed on the collimator model.

8. The neutron capture therapy system according to claim 1, further comprising a neutron beam generating unit for generating the neutron beam, wherein the neutron beam generating unit comprises an accelerator configured to accelerate a charged particle beam, a neutron beam generator reacting with the charged particle beam to generate the neutron beam, and a charged particle beam transmitter located between the accelerator and the neutron beam generator and configured to transmit the charged particle beam.

9. The neutron capture therapy system according to claim 6, wherein the base and the cantilever are both rectangular cuboids, the first shielding wall and the first wall are respectively provided with a fixing portion and a positioning portion which are respectively disposed around the collimator and the collimator model and adapted to fix the first auxiliary positioner and the second auxiliary positioner, wherein the neutron capture therapy system defines XYZ coordinates including a Y-axis parallel to the neutron beam axis, a Z-axis perpendicular to a ground, and an X-axis orthogonal to the Y-axis and the Z-axis, the fixing portion comprising a first fixing portion located right above the collimator and arranged in parallel to the X-axis, a second fixing portion located on a left side of the collimator and arranged in parallel to the Z-axis, and a third fixing portion located on a right side of the collimator and arranged parallel to the Z-axis, the positioning portion comprising a first positioning portion, a second positioning portion, and a third positioning portion respectively disposed corresponding to the first fixing portion, the second fixing portion, and the third fixing portion, wherein a center of a projection of the collimator on the first shielding wall and a center of a projection of the collimator model on the first wall are respectively configured to be reference points, and wherein coordinate values of a center of the first fixing portion, the second fixing portion and the third fixing portion based on the reference points are respectively the same as coordinate values of a center of the first positioning portion, the second positioning portion and the third positioning portion based on the reference points.

10. The neutron capture therapy system according to claim 6, wherein the base is a hollow cylinder, the cantilever is a hexahedron disposed perpendicular to the base, the first shielding wall and the first wall are respectively provided with a fixing portion and a positioning portion for fixing the first auxiliary positioner and the second auxiliary positioner, wherein the neutron capture therapy system defines XYZ coordinates including a Y-axis parallel to the neutron beam axis, a Z-axis perpendicular to a ground, and an X-axis orthogonal to the Y-axis and the Z-axis, and the fixing portion and the positioning portion are hollow circular rings having an identical size and a center of a circle respectively the same as a center of a projection of the collimator on the first shielding wall and a center of a projection of the collimator model on the first wall.

11. The neutron capture therapy system according to claim 10, wherein the base is provided with an annular track on which the cantilever slides in a circumferential direction and a fastening member for fixing the cantilever at a predetermined position, and the cantilever is provided with a guiding portion fitting with the annular track and a clamping member fitting with the fastening member to fix the cantilever.

12. The neutron capture therapy system according to claim 6, wherein the base of the first auxiliary positioner is detachably mounted on the first shielding wall, and the base of the second auxiliary positioner is detachably mounted on the first wall.

13. The neutron capture therapy system according to claim 7, wherein the base of the first auxiliary positioner is detachably mounted on the collimator, and the base of the second auxiliary positioner is detachably mounted on the collimator model.

14. A neutron capture therapy system, comprising:
an irradiation room provided with a collimator for a neutron beam to be emitted,
a preparation room provided with a collimator model corresponding to the collimator, and
an auxiliary positioner disposed in the irradiation room and/or the preparation room, wherein the auxiliary positioner comprises a base and a cantilever extending from the base, and wherein the cantilever is provided with at least one laser emitter for emitting a laser beam,
wherein a position of the at least one laser emitter is selectable, and a relative position between the at least one laser emitter and the collimator corresponds to a relative position between the at least one laser emitter and the collimator model.

15. The neutron capture therapy system according to claim 14, wherein the base is detachably mounted to the irradiation room and/or the preparation room.

16. A neutron capture therapy system, comprising:
an irradiation room configured to irradiate an irradiated body with a neutron beam, wherein the irradiation room comprises a first shielding wall, and
an auxiliary positioner disposed in the irradiation room, wherein the auxiliary positioner includes a cantilever provided with at least one laser emitter for emitting a laser beam to position the irradiated body,
wherein a collimator is disposed on the first shielding wall, and the auxiliary positioner is detachably mounted on the first shielding wall or the collimator, and
wherein a position of the at least one laser emitter is selectable.

17. The neutron capture therapy system according to claim 16, wherein the auxiliary positioner further comprises a base from which the cantilever extends perpendicularly, and wherein the at least one laser emitter is disposed on the cantilever.

18. The neutron capture therapy system according to claim 17, wherein the base is detachably mounted on the irradiation room.

* * * * *